US012672818B2

(12) United States Patent
Chang et al.

(10) Patent No.: US 12,672,818 B2
(45) Date of Patent: Jul. 7, 2026

(54) ARTIFICIAL INTELLIGENCE-DRIVEN DYNAMIC ULTRASOUND SYSTEM AND METHOD FOR DETECTING SUBACROMIAL IMPINGEMENT

(71) Applicant: National Taiwan University, Taipei (TW)

(72) Inventors: Kai-Min Chang, Taipei (TW); Yi-Chung Shu, Taipei (TW); Che-Yu Lin, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 19/081,166

(22) Filed: Mar. 17, 2025

(65) Prior Publication Data
US 2025/0352134 A1 Nov. 20, 2025

(30) Foreign Application Priority Data
May 14, 2024 (TW) .................................. 113117716

(51) Int. Cl.
| | |
|---|---|
| *A61B 8/08* | (2006.01) |
| *A61B 5/00* | (2006.01) |
| *G06N 3/0464* | (2023.01) |
| *G06T 7/00* | (2017.01) |
| *G06V 10/25* | (2022.01) |
| (Continued) | |

(52) U.S. Cl.
CPC .............. *A61B 5/4576* (2013.01); *A61B 8/08* (2013.01); *G06N 3/0464* (2023.01); *G06V 10/25* (2022.01); *G06V 10/44* (2022.01); *G06V 10/764* (2022.01)

(58) Field of Classification Search
CPC .... A61B 5/4576; G06N 3/0464; G06N 3/045; G06N 3/08; G06V 10/44; G06V 10/25; G06V 10/764; G06V 10/82
See application file for complete search history.

(56) References Cited

FOREIGN PATENT DOCUMENTS

CN 112861849 A * 5/2021 ........... G06F 18/214

OTHER PUBLICATIONS

Shu et al., Deep learning algorithm for predicting subacromial motion trajectory Dynamic shoulder ultrasound analysis, Ultrasonics , vol. 134, Sep. 2023, 107057 (Year: 2023).*

* cited by examiner

*Primary Examiner* — Boniface N Nganga
(74) *Attorney, Agent, or Firm* — Troutman Pepper Locke LLP; Tim Tingkang Xia, Esq.

(57) ABSTRACT
An artificial intelligence-driven dynamic ultrasound system and method for detecting subacromial impingement are disclosed by the present disclosure. The system includes Faster R-CNN module including a ResNet50 architecture, a region proposal network architecture and a first fully connected layer. The Faster R-CNN module is communicated with a dynamic ultrasound image acquisition module and a 1D-CNN module. The dynamic ultrasound image acquisition module includes a high frequency linear transducer configured to be disposed on a position of a lateral edge of an acromioclavicular joint parallel to a scapula of a subject. The 1D-CNN module comprises a first one-dimensional convolution layer, a second one-dimensional convolution layer, a second fully connected layer, a third fully connected layer and a fourth fully connected layer. The 1D-CNN module is configured to output a probability of developing subacromial impingement syndrome by the second, the third and the fourth fully connected layer.

10 Claims, 5 Drawing Sheets

(51) Int. Cl.
| | | |
|---|---|---|
| *G06V 10/44* | (2022.01) | |
| *G06V 10/764* | (2022.01) | |
| *G16H 30/40* | (2018.01) | |
| *G16H 50/20* | (2018.01) | |

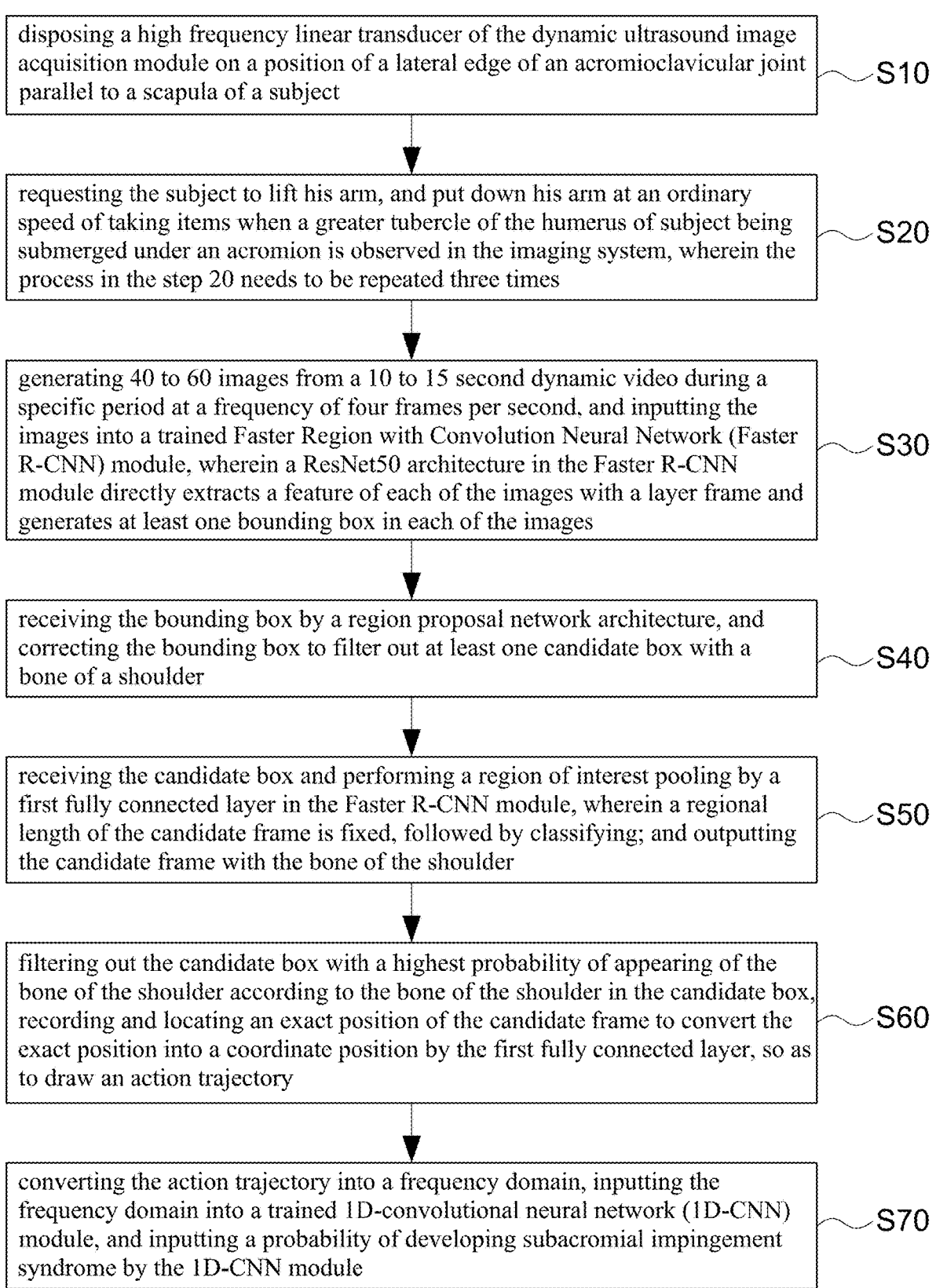

disposing a high frequency linear transducer of the dynamic ultrasound image acquisition module on a position of a lateral edge of an acromioclavicular joint parallel to a scapula of a subject ⟩~S10 requesting the subject to lift his arm, and put down his arm at an ordinary speed of taking items when a greater tubercle of the humerus of subject being submerged under an acromion is observed in the imaging system, wherein the process in the step 20 needs to be repeated three times ⟩~S20 generating 40 to 60 images from a 10 to 15 second dynamic video during a specific period at a frequency of four frames per second, and inputting the images into a trained Faster Region with Convolution Neural Network (Faster R-CNN) module, wherein a ResNet50 architecture in the Faster R-CNN module directly extracts a feature of each of the images with a layer frame and generates at least one bounding box in each of the images ⟩~S30 receiving the bounding box by a region proposal network architecture, and correcting the bounding box to filter out at least one candidate box with a bone of a shoulder ⟩~S40 receiving the candidate box and performing a region of interest pooling by a first fully connected layer in the Faster R-CNN module, wherein a regional length of the candidate frame is fixed, followed by classifying; and outputting the candidate frame with the bone of the shoulder ⟩~S50 filtering out the candidate box with a highest probability of appearing of the bone of the shoulder according to the bone of the shoulder in the candidate box, recording and locating an exact position of the candidate frame to convert the exact position into a coordinate position by the first fully connected layer, so as to draw an action trajectory ⟩~S60 converting the action trajectory into a frequency domain, inputting the frequency domain into a trained 1D-convolutional neural network (1D-CNN) module, and inputting a probability of developing subacromial impingement syndrome by the 1D-CNN module ⟩~S70

Fig. 5

ARTIFICIAL INTELLIGENCE-DRIVEN DYNAMIC ULTRASOUND SYSTEM AND METHOD FOR DETECTING SUBACROMIAL IMPINGEMENT

CROSS-REFERENCE TO RELATED APPLICATIONS

The present application claims priority to the benefit of Taiwan Patent Application Number 113117716 filed on May 14, 2024, the disclosure of which is incorporated herein by reference in its integrity.

FIELD OF THE INVENTION

The present disclosure relates to a dynamic ultrasound system, particularly, to an artificial intelligence-driven dynamic ultrasound system and method for detecting subacromial impingement.

BACKGROUND OF INVENTION

In daily life, in addition to sleeping time, upper limbs are in a state of long-term or repeated use. Overhead activity of the shoulder, especially repeated activity, are prone to shoulder problems.

The shoulder joint is the most mobile joint of the human body and is mainly composed of muscles, ligaments, joints, scapula, humerus, and clavicle. Joint stability and coordination are maintained through rotator cuff muscles, including supraspinatus, infraspinatus, subscapularis, and teres minor. Excessive use of the shoulder may lead to shoulder pain, which is one of the common pains in daily life. Shoulder pain can occur due to various reasons, such as rotator cuff tears, frozen shoulder, and subacromial impingement syndrome. Among these, subacromial impingement syndrome accounts for 44% to 65% of causes of shoulder pain.

Currently, many cases of shoulder pain with difficulty lifting the arm above the horizontal plane are often misdiagnosed as frozen shoulder. However, causes of subacromial impingement syndrome differ from those of frozen shoulder. Specifically, subacromial impingement syndrome is caused by a structural narrowing of the subacromial space lying underneath the acromion, the coracoid process, the acromioclavicular joint and the coracoacromial ligament, resulting in excessive or repetitive contact between the greater tuberosity of the humeral head and the lower edge of the acromion, leading to rotator cuff syndrome and subacromial-subdeltoid bursitis. The pain caused by subacromial impingement syndrome often occurs during forward elevation of the arm ranging from 60° to 120°, which is a distinctive feature of subacromial impingement syndrome.

In practice, a functional diagnostic method for the assessment of subacromial impingement syndrome comprises the following criteria: (1) unilateral or bilateral shoulder pain occurring during exercise indicated by a Visual Analogue Scale score of ≥4; (2) at least one positive result of Neer's test, Hawkins-Kennedy test, and painful arc test for shoulder; and (3) pain lasting for more than 3 weeks. A pathologic diagnosis for subacromial impingement syndrome can be further conducted through diagnostic imaging examinations.

The diagnostic imaging examinations comprise musculoskeletal ultrasound examinations for detecting whether there is inflammation or tearing in tissues, such as rotator muscles and bursae. Further, ultrasound can be used to confirm whether the subacromial space is squeezed, and an X-ray can be utilized to assess a distance between the acromion and the humerus and whether the acromion is squeezed or impinged upon the rotator cuff.

However, an acromion-humerus distance ratio is not consistent for each person regardless of subacromial impingement syndrome. In a static ultrasound examination, an arm is fixed at a certain angle and the examination is performed in a static state, rather than in actual motion, resulting in less accurate examination results. Therefore, during static ultrasound examinations, medical personnel must analyze ultrasound images, leading to drawbacks such as high labor costs, extensive technical resources, time consumption, and a lack of objective and comprehensive evaluation. As mentioned above, the conventional devices and methods for detecting subacromial impingement need to be improved.

SUMMARY OF THE INVENTION

Therefore, an object of the present disclosure is to provide an artificial intelligence-driven dynamic ultrasound system and method for detecting subacromial impingement, which can provide objective assessments and reduce labor costs and technically resource.

Disclosed herein is an exemplary artificial intelligence-driven dynamic ultrasound system for detecting subacromial impingement, including: a Faster Region with Convolution Neural Network (Faster R-CNN) module, including: a ResNet50 architecture, configured to extract a feature of an input image of a target and to generate a plurality of bounding boxes in the input image; a region proposal network (RPN) architecture, configured to perform a filtering procedure; and a first fully connected layer, configured to perform a classification procedure, so as to output a candidate box with a highest probability of the target appearing, and configured to draw an action trajectory, wherein the Faster R-CNN module is communicated with a dynamic ultrasound image acquisition module and a 1D-convolutional neural network (1D-CNN) module, wherein the dynamic ultrasound image acquisition module at least includes a high frequency linear transducer configured to be disposed on a position of a lateral edge of the acromioclavicular joint parallel to a scapula of a subject, so as to obtain a 10 to 15 second dynamic video during a specific period, wherein the 1D-CNN module comprises a first one-dimensional convolution layer, a second one-dimensional convolution layer, a second fully connected layer, a third fully connected layer, and a fourth fully connected layer, the 1D-CNN module is trained using a Rectified Linear Unit (ReLU), and is configured to output a probability of developing subacromial impingement syndrome by the second fully connected layer, the third fully connected layer, and the fourth fully connected layer.

In another embodiment, the ResNet50 architecture is configured to directly extract the feature from the input image by a layer framework.

In another embodiment, a frequency of the high frequency linear transducer ranges from 10 to 18 megahertz (MHz).

In another embodiment, the 1D-CNN module is trained according to a subject database comprising data of recognition of the subacromial impingement syndrome. Preferably, the data may be confirmed by healthcare professionals through manual positioning and diagnosis.

Disclosed herein is an exemplary artificial intelligence-driven dynamic ultrasound method for detecting subacromial impingement, comprising the following steps of:

(a) generating 40 to 60 images from a 10 to 15 second dynamic video during a specific period at a frequency of four frames per second, and inputting the images into a trained Faster Region with Convolution Neural Network (Faster R-CNN) module, wherein a ResNet50 architecture in the Faster R-CNN module directly extracts a feature of each of the images with a layer frame and generates at least one bounding box in each of the images;

(b) receiving the bounding box by a region proposal network (RPN) architecture, and correcting the bounding box to filter out at least one candidate box with a bone of a shoulder;

(c) receiving the candidate box and performing a region of interest pooling (ROI pooling) by a first fully connected layer in the Faster R-CNN module, wherein a regional length of the candidate frame is fixed, followed by classifying; and outputting the candidate frame with the bone of the shoulder;

(d) filtering out the candidate box with a highest probability of appearing of the bone of the shoulder according to the bone of the shoulder in the candidate box, recording and locating an exact position of the candidate frame to convert the exact position into a coordinate position by the first fully connected layer, so as to draw an action trajectory; and (e) converting the action trajectory into a frequency domain, inputting the frequency domain into a trained 1D-convolutional neural network (1D-CNN) module, and inputting a probability of developing subacromial impingement syndrome by the 1D-CNN module.

In another embodiment, the step (a) generates the dynamic video using the following steps of:

in the step (a) the dynamic video is generated by using the following steps of:

(a1) disposing a high frequency linear transducer of the dynamic ultrasound image acquisition module on a position of a lateral edge of an acromioclavicular joint parallel to a scapula of a subject; and (a2) observing a greater tuberosity of a humerus of the subject by an imaging system when an arm of the subject is in a lifted state, wherein the lifted state is sustained until the greater tuberosity being submerged under an acromion is observed, wherein the step of (a2) is repeated at least once.

In another embodiment, the bone of the shoulder in the step (c) includes a greater tubercle of a humerus and a lateral edge of an acromion.

In another embodiment, the action trajectory in the step (d) is created by the following steps: calculating a vertical relative distance according to a coordinate position of the bone of the shoulder in the dynamic video, and projecting a component vector of the vertical relative distance onto a position-time curve.

In another embodiment, the frequency domain in the step (e) is obtained by converting the action trajectory with a fast Fourier transform.

In another embodiment, the 1D-CNN module in the step (e) is trained by using a rectified linear unit between a first 1D convolution layer and a second 1D convolution layer, and is configured to output a probability of developing subacromial impingement syndrome.

BRIEF DESCRIPTION OF THE DRAWINGS

FIG. 5 is a schematic flow chart of the artificial intelligence-driven dynamic ultrasound method for detecting subacromial impingement in accordance with an embodiment.

DESCRIPTION OF THE PREFERRED EMBODIMENTS

Figure 1:
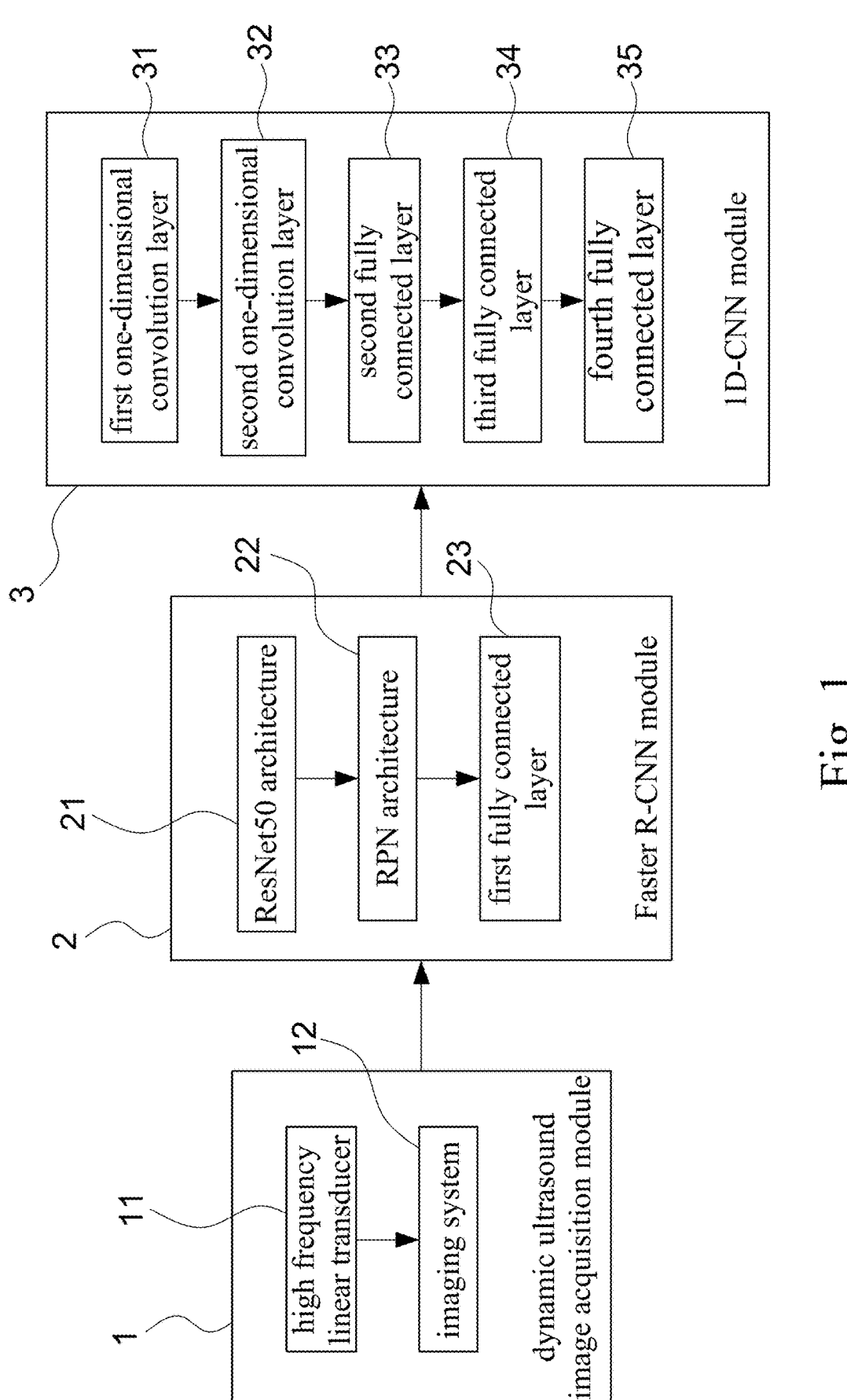
FIG. 1 is a schematic diagram of an artificial intelligence-driven dynamic ultrasound system for detecting subacromial impingement in accordance with an embodiment.

Refer to FIG. 1 to FIG. 4. According to an exemplary embodiment of the present disclosure, a system for artificial intelligence-driven dynamic ultrasound to detect subacromial impingement includes a dynamic ultrasound image acquisition module 1, a Faster Region with Convolution Neural Network (Faster R-CNN) module 2, and a 1D-Convolutional Neural Network (1D-CNN) module 3. The dynamic ultrasound image acquisition module 1 includes a high frequency linear transducer 11 and an imaging system 12. The dynamic ultrasound image acquisition module 11 is configured to disposed on a position of a lateral edge of an acromioclavicular joint parallel to a scapula of a subject for acquiring a dynamic video during a specific period (e.g., 10 to 15 seconds). The dynamic ultrasound image acquisition module 1 is communicated with the Faster R-CNN module 2. The Faster R-CNN module 2 includes a ResNet50 architecture 21, a Region Proposal Network (RPN) architecture 22, and a first fully connected layer 23. A feature from an input image 4 of a target is extracted by The ResNet50 architecture 21, and a plurality of bounding boxes 52 in the input image are generated, followed by a plurality of feature maps 5. Subsequently, a classification procedure is performed on the feature maps 5 by the first fully connected layer 23, and then a plurality of candidate frames are input. The Faster R-CNN module 2 is communicated with the dynamic ultrasound image acquisition module 1 and the 1D-CNN module 3. The 1D-CNN module 3 is connected to the Faster R-CNN module 2, and includes a first one-dimensional convolution layer 31, a second one-dimensional convolution layer 32, a second fully connected layer 33, a third fully connected layer 34, and a fourth fully connected layer 35. A rectified linear unit (ReLU) is used for model training between the first one-dimensional convolution layer 31 and the second one-dimensional convolution layer 32. Finally, a probability of developing subacromial impingement syndrome is output by the second fully connected layer 33, the third fully connected layer 34, and the fourth fully connected layer. 35

FIG. 1 is a schematic diagram of the artificial intelligence-driven dynamic ultrasound system for detecting subacromial impingement in accordance with an embodiment of the present disclosure. In the present embodiment, the dynamic ultrasound image acquisition module 1 includes a high frequency linear transducer 11 with a frequency ranging from 10 to 18 megahertz (MHz).

In another embodiment of the present disclosure, the 1D-CNN module is trained according to a subject database comprising data of recognition of the subacromial impingement syndrome. The data may be confirmed by healthcare professionals through manual positioning and diagnosis. Specifically, the ultrasound images are firstly positioned by the healthcare professionals manually in advance, followed by determining subacromial impingement syndrome, and finally the data are stored in the subject database for performing a model training onto a one-dimensional convolutional neural network module.

Figure 2:
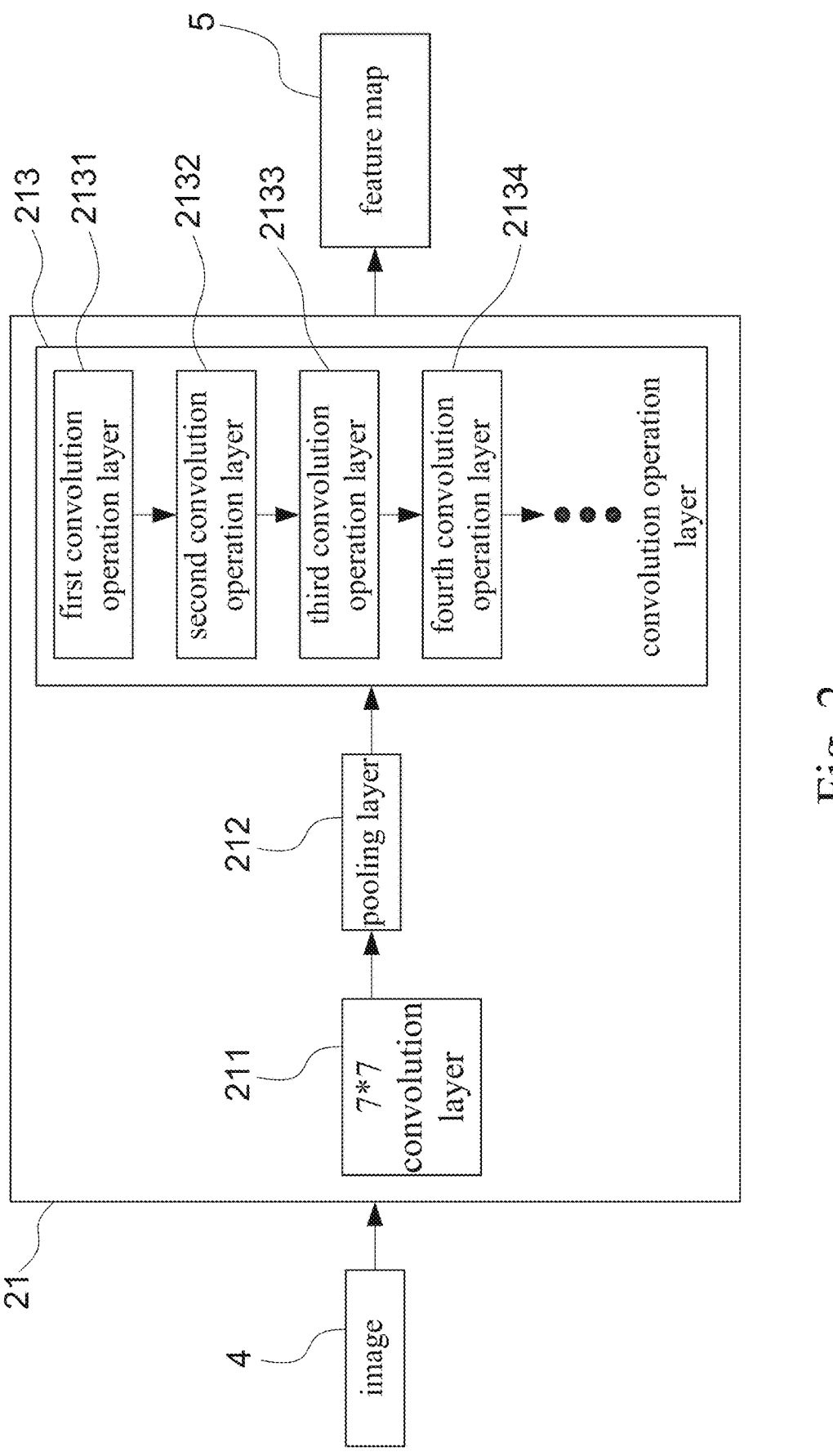
FIG. 2 is a schematic diagram of the ResNet50 architecture in accordance with an embodiment.
Figure 3:
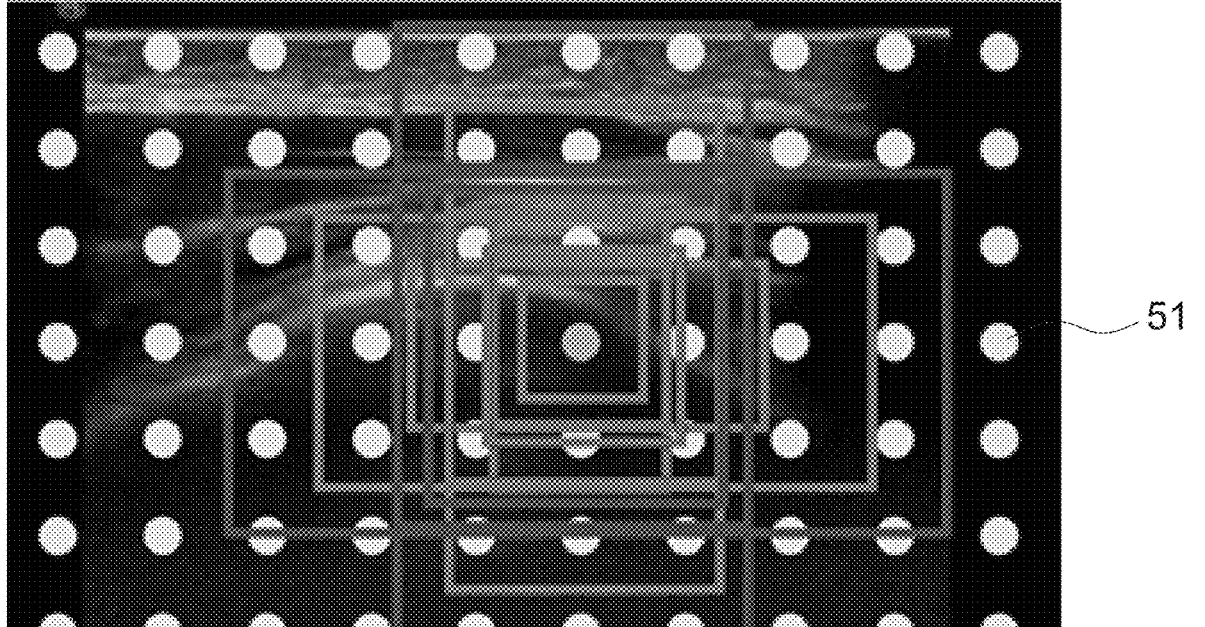
FIG. 3 is a schematic diagram of multiple bounding boxes generated by the ResNet50 architecture in accordance with an embodiment.

Refer to FIG. 2. In another exemplary embodiment of the present disclosure, the ResNet50 architecture 21 includes a 7*7 convolution layer 211, a pooling layer 212, and a convolution operation layer 213. The ResNet50 architecture 21 is capable of directly extracting features from the input image 4 using the layer framework.

Refer to FIG. 5. In another exemplary embodiment of the present disclosure, an artificial intelligence-driven dynamic ultrasound method for detecting subacromial impingement comprises the following steps of S10 to S70.

In step S10, a high frequency linear transducer 11 of the dynamic ultrasound image acquisition module 1 is disposed on a position of a lateral edge of an acromioclavicular joint parallel to a scapula of a subject.

In step S20, the subject is requested to lift his arm, and put down his arm at an ordinary speed of taking items when a greater tubercle of the humerus of subject being submerged under an acromion is observed in the imaging system 12. The process in the step 20 needs to be repeated at least once.

In step S30, a specific number (e.g., 40 to 60 frames) of images are created from a dynamic video of a specific period (e.g., 10 to 15 seconds) at a frequency of four frames per second. Afterwards, the aforementioned specific number of images are input into the trained Faster R-CNN module 2. The ResNet50 architecture 21 in the Faster R-CNN module 2 may directly extract features of the image 4 with a layer frame, and generate multiple feature maps 5 as well as at least one bounding box 52 therein.

In step S40, the RPN architecture 22 receives and corrects the bounding box 52, and filters out at least one candidate box containing a bone of a shoulder.

In step S50, the first fully connected layer 23 receives the candidate box, performs a region of interest pooling (ROI pooling) operation, in which a regional length of the candidate frame is fixed, and conducts a classification, thereby outputting the candidate frame with the bone of the shoulder.

In step S60, the candidate box with a highest probability of appearing of the bone of the shoulder is filtered out according to the bone of the shoulder in the candidate box. By the first fully connected layer 23, an exact position of the candidate frame is recorded and located, and the exact position is converted into a coordinate position, so as to draw an action trajectory.

In step S70, the action trajectory is converted into a frequency domain, and the frequency domain is input into a trained 1D-convolutional neural network (1D-CNN) module 3. A probability of developing subacromial impingement syndrome is input by the 1D-CNN module 3.

In another exemplary embodiment of the present disclosure, step S20 is repeated more than three times to avoid extreme values due to uneven force output from the active movement of the shoulder.

Refer to FIG. 1 to FIG. 3 and FIG. 5. In another exemplary embodiment of the present disclosure, the ResNet50 architecture 21 includes a 7*7 convolution layer 211, a pooling layer 212, and a convolution operation layer 213. The convolution operation layer 213 includes a first convolution operation layer 2131, a second convolution operation layer 2132, a third convolution operation layer 2133, and a fourth convolution operation layer 2134. In step S30, the convolution operation layer 213 may multiply sliding weights of the image 4 and extract features to generate 7*10 feature points 51 and 2048 channels on a feature map 5. Accordingly, a size of the feature map 5 is 7*10*2048 pixels. Further, several bounding boxes 52 are generated on the feature map 5. In a single channel, the bounding boxes 52 with three different aspect ratios are generated on each feature point 51 of the feature map 5. Accordingly, there are 9 (3*3) different sizes of bounding boxes 52 on any feature point 51. 630 (7*10*9) bounding boxes 52 are generated in an image finally.

Figure 4:
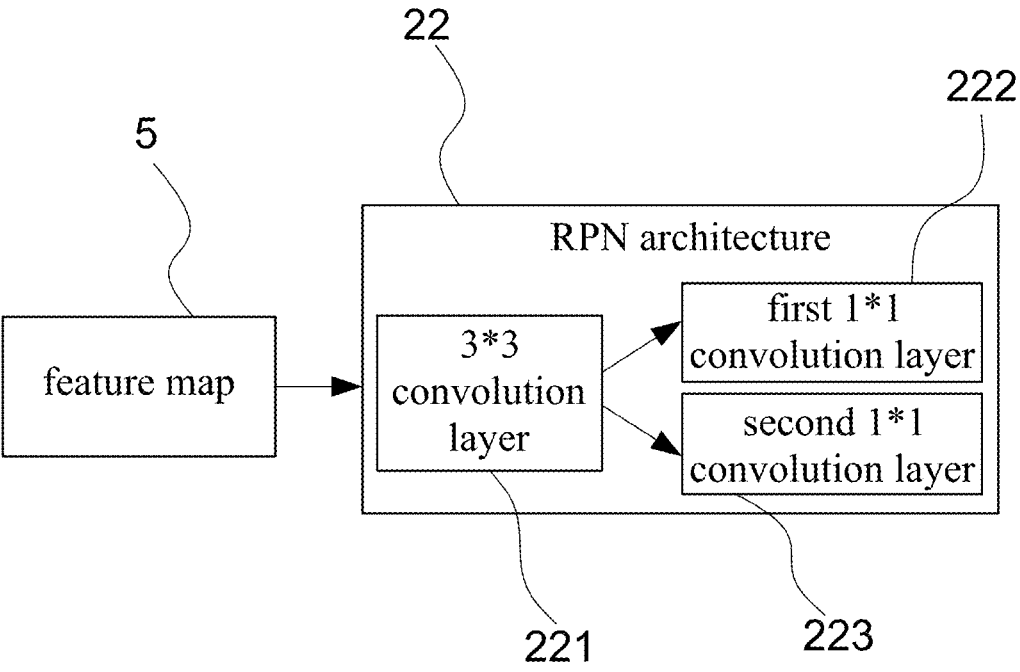
FIG. 4 is a schematic diagram of the region proposal network (RPN) architecture in accordance with an embodiment.

Refer to FIG. 1, FIG. 4 and FIG. 5. In another exemplary embodiment of the present disclosure, in step S40, information of the bounding box 52 is transmitted to the RPN architecture 22 after the bounding box 52 is generated. In the exemplary embodiment, the RPN architecture 22 contains multiple convolutional layers. In order to perform feature integration, 256 channels are generated by the feature map 5 through the 3*3 convolution layer 221. Subsequently, two paths are performed simultaneously. In an upper path, 18 channel are output by the first 1*1 convolution layer 222. In other word, nine bounding boxes 52 are generated by a feature point 51 on the feature map 5, and each bounding box 52 may or may not contain the shoulder bone that refers to a greater tubercle of a humerus and a lateral edge of an acromion. Accordingly, a total of 9*2 (i.e., 18) possibilities are obtained. In the exemplary embodiment, in a lower path, an offset of the bounding box 52 is calculated through the second 1*1 convolution layer 223, and 36 channel are output. In other words, each feature point 51 on the lower path has nine bounding boxes 52, and each bounding box 52 has four offsets. Accordingly, the offset on one feature point 51 has 9*4 (i.e., 36) values, an image size of a single channel is 7*10, and a size of the resultant feature map 5 is 7*10*36 pixels. Finally, the bounding box 52 containing the shoulder bone with the highest probability is output by the first 1*1 convolution layer 222, and the corresponding offset in the second 1*1 convolution layer 223 based on these bounding boxes 52 may be found out, so as to correct the bounding box 52. A total of 300 candidate boxes are finally screened out.

Refer to FIG. 1 and FIG. 5. In other exemplary embodiments, the action trajectory drawn by the first fully connected layer 23 in step S60 is calculated by adding time seconds (i) to the vertical distance coordinates of the acromion $(x_1, y_1)$ and the greater tuberosity of the humerus $(x_2, y_2)$, and the formula is shown as follows:

$$Y^i_{action\ trajectory} = y^i_1 - y^i_2; I = 0 \sim n.$$

In another exemplary embodiment of the present disclosure, the action trajectory drawn by the first fully connected layer 23 is converted into the frequency domain through Fast Fourier Transform (FFT), and then the frequency domain is input into the 1D-CNN module 3 described in step S70. The features of the action trajectory are extracted by the first one-dimensional convolution layer 31 and the second one-dimensional convolution layer 32 through sliding weights, which is beneficial to control and confirm the characteristics of the action trajectory. A rectified linear unit (ReLU) is utilized between the first one-dimensional convolution layer 31 and the second one-dimensional convolution layer 32 for model training, so as to avoid generation of excessive unnecessary information. Finally, each feature point 51 is identified through the second fully connected layer 33, the third fully connected layer 34, and the fourth fully connected layer 35, so as to input the probability of developing subacromial impingement syndrome.

As mentioned above, the artificial intelligence-driven dynamic ultrasound system and method of the present disclosure can provide a more objective assessment, which is conducive to assess the probability of developing subacromial impingement syndrome. In addition, the labor costs, technical resources and time for diagnosis of subacromial impingement can be reduced by the artificial intelligence-driven dynamic ultrasound system and method of the present disclosure.

While this invention has been described with respect to at least one embodiment, the invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An artificial intelligence-driven dynamic ultrasound system for detecting subacromial impingement, comprising:
a Faster Region with Convolution Neural Network (Faster R-CNN) module, including:
a ResNet50 architecture, configured to extract a feature of an input image of a target and to generate a plurality of bounding boxes in the input image;
a region proposal network (RPN) architecture, configured to perform a filtering procedure; and
a first fully connected layer, configured to perform a classification procedure, so as to output a candidate box with a highest probability of the target appearing, and configured to draw an action trajectory,
wherein the Faster R-CNN module is communicated with a dynamic ultrasound image acquisition module and a 1D-convolutional neural network (1D-CNN) module,
wherein the dynamic ultrasound image acquisition module at least includes a high frequency linear transducer configured to be disposed on a position of a lateral edge of an acromioclavicular joint parallel to a scapula of a subject, so as to obtain a dynamic video during a specific period,
wherein the 1D-CNN module comprises a first one-dimensional convolution layer, a second one-dimensional convolution layer, a second fully connected layer, a third fully connected layer, and a fourth fully connected layer, the 1D-CNN module is trained using a Rectified Linear Unit (ReLU), and is configured to output a probability of developing subacromial impingement syndrome by the second fully connected layer, the third fully connected layer, and the fourth fully connected layer.

2. The artificial intelligence-driven dynamic ultrasound system for detecting subacromial impingement of claim 1, wherein the ResNet50 architecture is configured to directly extract the feature from the input image by a layer framework.

3. The artificial intelligence-driven dynamic ultrasound system for detecting subacromial impingement of claim 1, wherein a frequency of the high frequency linear transducer ranges from 10 to 18 megahertz (MHz).

4. The artificial intelligence-driven dynamic ultrasound system for detecting subacromial impingement of claim 1, wherein the 1D-CNN module is trained according to a subject database comprising data of recognition of the subacromial impingement syndrome.

5. An artificial intelligence-driven dynamic ultrasound method for detecting subacromial impingement, comprising the following steps of:

(a) generating a specific number of images from a dynamic video during a specific period at a frequency of four frames per second, and inputting the images into a trained Faster Region with Convolution Neural Network (Faster R-CNN) module, wherein a ResNet50 architecture in the Faster R-CNN module directly extracts a feature of each of the images with a layer frame and generates at least one bounding box in each of the images;

(b) receiving the bounding box by a region proposal network (RPN) architecture, and correcting the bounding box to filter out at least one candidate box with a bone of a shoulder;

(c) receiving the candidate box and performing a region of interest pooling (ROI pooling) by a first fully connected layer in the Faster R-CNN module, wherein a regional length of the candidate frame is fixed, followed by classifying; and outputting the candidate frame with the bone of the shoulder;

(d) filtering out the candidate box with a highest probability of appearing of the bone of the shoulder according to the bone of the shoulder in the candidate box, recording and locating an exact position of the candidate frame to convert the exact position into a coordinate position by the first fully connected layer, so as to draw an action trajectory; and e) converting the action trajectory into a frequency domain, inputting the frequency domain into a trained 1D-convolutional neural network (1D-CNN) module, and outputting a probability of developing subacromial impingement syndrome by the 1D-CNN module.

6. The artificial intelligence-driven dynamic ultrasound method for detecting subacromial impingement of claim 5, wherein in the step (a) the dynamic video is generated by using the following steps of:
(a1) disposing a high frequency linear transducer of the dynamic ultrasound image acquisition module on a position of a lateral edge of an acromioclavicular joint parallel to a scapula of a subject; and
(a2) observing a greater tuberosity of a humerus of the subject by an imaging system when an arm of the subject is in a lifted state, wherein the lifted state is sustained until the greater tuberosity being submerged under an acromion is observed,
wherein the step of (a2) is repeated at least once.

7. The artificial intelligence-driven dynamic ultrasound method for detecting subacromial impingement of claim 5, wherein the bone of the shoulder in the step (c) includes a greater tubercle of a humerus and a lateral edge of an acromion.

8. The artificial intelligence-driven dynamic ultrasound method for detecting subacromial impingement of claim 5, wherein the action trajectory in the step (d) is created by the following steps: calculating a vertical relative distance according to a coordinate position of the bone of the shoulder in the dynamic video, and projecting a component vector of the vertical relative distance onto a position-time curve.

9. The artificial intelligence-driven dynamic ultrasound method for detecting subacromial impingement of claim 5, wherein the frequency domain in the step (e) is obtained by converting the action trajectory with a fast Fourier transform.

10. The artificial intelligence-driven dynamic ultrasound method for detecting subacromial impingement of claim 5, wherein the 1D-CNN module in the step (e) is trained by using a rectified linear unit between a first 1D convolution layer and a second 1D convolution layer, and is configured to output a probability of developing subacromial impingement syndrome.

* * * * *